(12) United States Patent
Zembower et al.

(10) Patent No.: US 6,225,481 B1
(45) Date of Patent: May 1, 2001

(54) ROBUSTAFLAVONE, INTERMEDIATES AND ANALOGUES AND METHOD FOR PREPARATION THEREOF

(75) Inventors: David E. Zembower, La Grange; Heping Zhang, Elmhurst; Michael T. Flavin, Darien; Yuh-Meei Lin, Naperville, all of IL (US)

(73) Assignee: Advanced Life Sciences, Inc., Lemont, IL (US)

( * ) Notice: Subject to any disclaimer, the term of this patent is extended or adjusted under 35 U.S.C. 154(b) by 0 days.

(21) Appl. No.: 09/137,767

(22) Filed: Aug. 21, 1998

Related U.S. Application Data

(60) Provisional application No. 60/057,131, filed on Aug. 28, 1997, and provisional application No. 60/081,699, filed on Apr. 14, 1998.

(51) Int. Cl.$^7$ .................................................. C07D 311/76
(52) U.S. Cl. .............................................................. 549/402
(58) Field of Search ............................................ 549/402

(56) References Cited

PUBLICATIONS

Lin, Y.M. et al., (1977) *Bioorg. Med. Chem. Lett.*, 7, 2325–2328.
Hoofnagle, J.H. et al., (1990), *N. Engl. J. Med.*, 323, 337–339.
Aach, R.D., (1988), *Ann Intern. Med.*, 109, 89–91.
Martin, P. et al., (1992), *Innovations in Antiviral Development and the Detection of Virus Infections*, Plenum Press, New York, pp. 111–120.
Maynard, J.E. et al., (1989), *Rev. Infect. Dis.*, 11, S574–S578.
Varshney, A.K., (1979) *Experimentia*, 29, 784–786.
Lin, Y.–M. et al., (1974), *Phytochem.*, 13, 1617–1619.
Miyaura, N. et al., (1995), *Chem. Rev.*, 95, 2457–2483.
Muller, D. et al., (1991), *Tetrahedron Lett.*, 32, 2229–2232.
Nakazawa, K., (1962), *Chem. Pharm. Bull.*, 10, 1032–1038.
Hutchins, W.A. et al., (1939), *J. Chem. Soc.*, 91–94.
Chang, C.T. et al., (1961), *J. Org. Chem.*, 26, 3142–3143.
Ahmad, S., et al., (1972), *Pak. J. Sci. Ind. Res.*, 15, 361–362.
Cambie, R. C. et al., (1976), *J. Chem. Soc. Perkin Trans. I*, 1161–1164.
Stille, J.K., (1986), *Angew. Chem. Int. Ed. Eng.*, 25, 508–524.
Azizian, H. et al., (1981), *J. Organomet. Chem.*, 215, 49–58.
Ishiyama, T. et al., (1995), *J. Org. Chem.*, 60, 7508–7510.
Brotherton, R.J., et al., (1960), *J. Am. Chem. Soc.*, 82, 6242–6245.
Noth, H.Z., (1984), *Naturforsch*, 39b, 1463–1466.
Johnson, M.G., et al., (1997) *Tetrahedron Lett.*, 38, 7001–7002.
Wessely, F. et al., (1930) *Monatsch. Chem.*, 56, 97–105.
Zembower, D.E., et al., (1998) *Antiviral Res.* In press.
Roy, D. et al., (1980), *Indian J. Chem.*, 19B, 583–586.
Schmid, L. et al., (1928) *Monatsch. Chem.*, 49, 83–91.
Dawson, R. M. et al., (1965) *J. Aust. J. Chem.*, 18, 1871–1875.
Miyaura, N., et al., (1995) *Chem. Rev.*, 95, 2457–2483.
Stille, J.K. et al., (1986) *Chem. Int. Ed. Eng.*, 25, 508–524.
Marcoux, J. F. et al., (1997) *J. Org. Chem.*, 62, 1568–1569.
Dean, F.M. et al., (1966) *Tetrahedron Lett.*, 4153–4159.
Heck, Richard, (1985) *Palladium Reagents In Organic Synthesis.*, Academic Press, London.
Murata, M. et al., (1977) *J. Org. Chem.*, 62, 6458–6459.
Hoofnagle et al., (1997) *J. Viral Hepatitis*, 4(Suppl. 1), 41–50.
Mao et al., (1997) *Chemical Abstracts*, vol. 127, No. 21, pp. 656 Abstract No. 293018c.

*Primary Examiner*—John Kight
*Assistant Examiner*—Raymond Covington
(74) *Attorney, Agent, or Firm*—McDonnell Boehnen Hulbert & Berghoff

(57) ABSTRACT

Robustaflavone, intermediates and analogues thereof and a method for synthesizing the same are provided. The method involves constructing apigenin ethers containing functionalities at the 6- and 3'-positions which could be cross-coupled using transition metal catalysis. The method also involves development of a regioselective iodination of an apigenin derivative at the 6-position, formation of an apigenin 3'-boronate using a palladium-catalyzed exchange of the corresponding 3'-iodide with a diboron reagent. Finally, Suzuki coupling to form the sterically congested 6-3'" biaryl bond of robustaflavone provides access to the desired biflavanoid system. Robustaflavone intermediates and analogues may be used to prepare analogues of other biflavanoids such as hinokifavone, rhusflavone and succedaneaflavone.

23 Claims, No Drawings

ROBUSTAFLAVONE, INTERMEDIATES AND ANALOGUES AND METHOD FOR PREPARATION THEREOF

CROSS-REFERENCE

This application claims the benefit of provisional application serial number 60/057,131, filed Aug. 28, 1997, and 60/081,699, filed Apr. 14, 1998.

Portions of this work were funded under Small Business Innovation Research grant 1R43 AI40745-01, by the National Institutes of Health. Thus, the United States government has certain rights to this invention.

FIELD OF THE INVENTION

The present invention relates to the robustaflavone, intermediates for preparing robustaflavone, and robustaflavone analogues as well as compositions containing the same. The present invention also relates to synthesis of robustaflavone, intermediates and analogues thereof.

BACKGROUND OF THE INVENTION

Robustaflavone, a naturally occurring biflavanoid, is a potent non-nucleoside inhibitor of hepatitis B virus (HBV) replication[1]. HBV is one of the most serious health problems in the world today, and is listed as the ninth leading cause of death by the World Health Organization[2]. Approximately 300 million persons are chronically infected with HBV worldwide, with over one million of those in the United States. The Centers for Disease Control estimates that over 300,000 new cases of acute HBV infection occurs in the United States each year, resulting in 4,000 deaths due to cirrhosis and 1,000 due to hepatocellular carcinoma[3]. The highest incidence of HBV infection occurs in the Far East and sub-Saharan Africa, where approximately 20% of the population are chronically infected[4]. Infection can be prevented through the use of several extremely effective recombinant vaccines[5]. Despite the availability of these vaccines, HBV infection remains the most significant viral pathogen infecting man, particularly in under-developed countries.

Preliminary in vitro evaluations had shown that robustaflavone possesses anti-hepatitis B activity comparable to several nucleoside analogues currently in clinical trialsl, as well as acts synergistically with these agents[22]. Robustaflavone was first[6] isolated in 1973, as its hexa-O-methyl ether, from leaf extracts of *Agathis robusta*, and later[7] in larger quantities from the seed-kernels of *Rhus succedanea*. While robustaflavone represents an important lead compound in the search for potential anti-hepatitis B agents, no total synthesis of robustaflavone has been reported to date. A recent synthesis of a related biflavanoid, amentoflavone (I8,II3'-biapigenin), which consists of two apigenin units connected via a biaryl linkage between respective 8- and 3'-positions, was achieved using Suzuki coupling[8] of an apigenin 8-boronic acid derivative with an appropriate 3'-iodoapigenin analogue[9]. However, there is no disclosure or suggestion that this approach can be extended to the total synthesis of robustaflavone.

SUMMARY OF THE INVENTION

The present invention relates to a method for preparing robustaflavone, a biologically active biflavanoid composed of two apigenin (5,7,4'-trihydroxyflavone) units connected via a biaryl linkage between their 6- and 3'-positions. The present invention also relates to robustaflavone intermediates and analogues useful as potential antiviral agents and/or for preparing other biflavanoids and method for preparing the

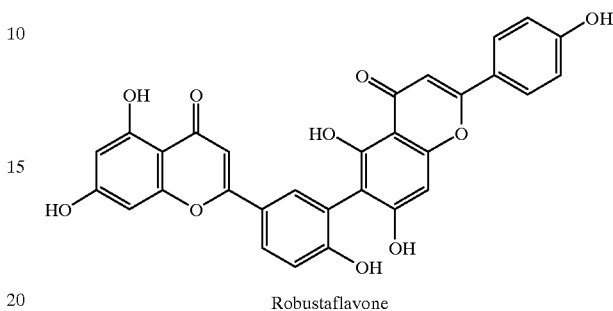
Robustaflavone

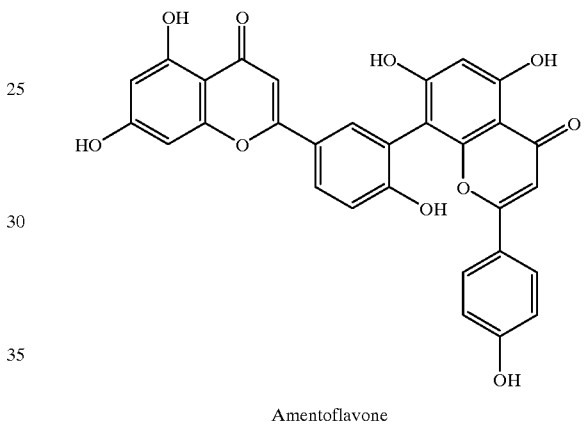
Amentoflavone same. The method of the present invention includes a thallium-assisted regioselective iodination of apigenin 7,4'-dimethyl ether in the 6-position, allowing efficient access to 6-iodoapigenin trimethyl ether (8). See Scheme 2. This step allows for an efficient route to 6-halogenated flavones that has not been described previously. Another step in the method of the invention entails conversion of 3'-iodoapigenin trimethyl ether (5a) to its corresponding 3'-pinacol boronate derivative 9b, via the palladium-catalyzed cross-coupling of 5a with bis(pinacolato)diboron. See Scheme 3. The corresponding 3'-stannane 9a failed to couple with iodide 8 under Stille conditions, and attempts to convert either of iodides 5a or 8 to their corresponding boronic acids using standard methods (halogen-lithium exchange/trialkylborate quench) failed. See Scheme 3. Identification of reaction conditions which allowed Suzuki coupling between boronate 9b with iodide 8 furnished the critical 6-3' biaryl linkage, to afford the desired robustaflavone skeleton in the form of its hexamethyl ether (10). See Scheme 4. Finally, demethylation under non-aqueous conditions using $BBr_3$ provided access to synthetic robustaflavone, which was identical in all respects to the natural product. See Scheme 4. The method of the present invention will allow access to needed quantities of robustaflavone for further biological studies, as well as provide an efficient method for the synthesis of intermediates and structural analogues.

Accordingly, it is one object of the invention to provide a direct method for preparing robustaflavone, intermnediates and analogues thereof.

It is another object of the invention to provide intermediates useful in preparing robustaflavone analogues and other biflavanoid compounds having linkages through the 6-position or the 3' position such as hinokiflavane, rhusflavone and succedaneaflavone.

It is a further object of the invention to provide robustaflavone analogues useful as potential anti-viral, e.g., anti-hepatitis B virus, agents.

These and other objects of the invention will become apparent in light of the detailed description below.

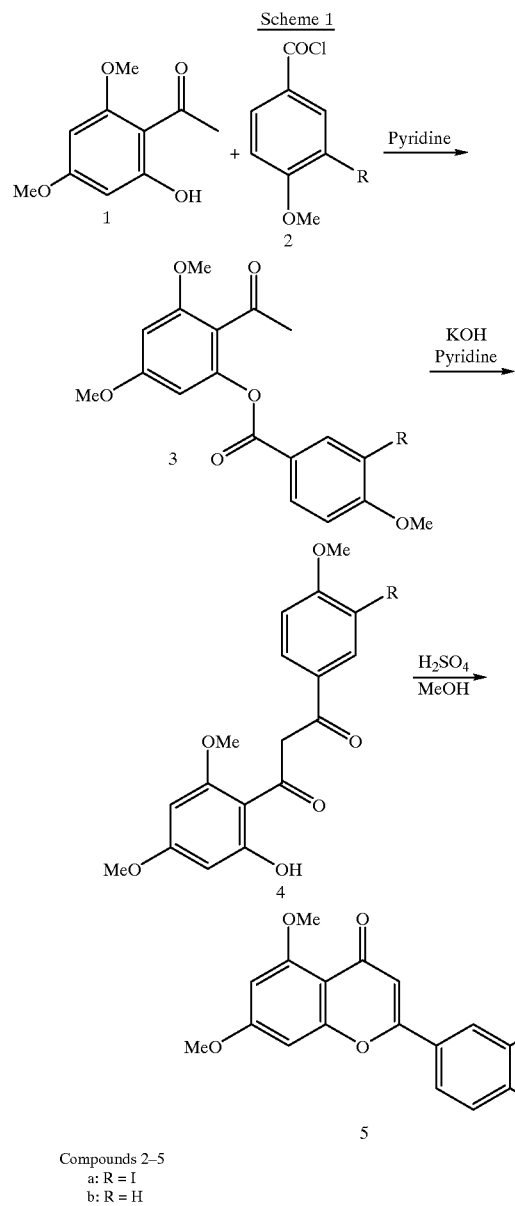

Compounds 2–5
a: R = I
b: R = H

Scheme 2

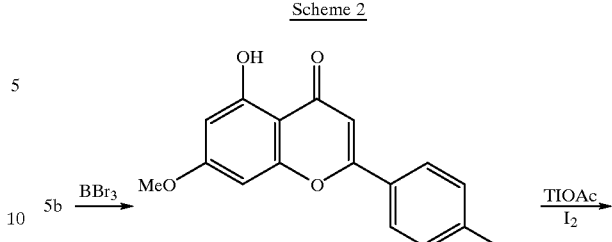

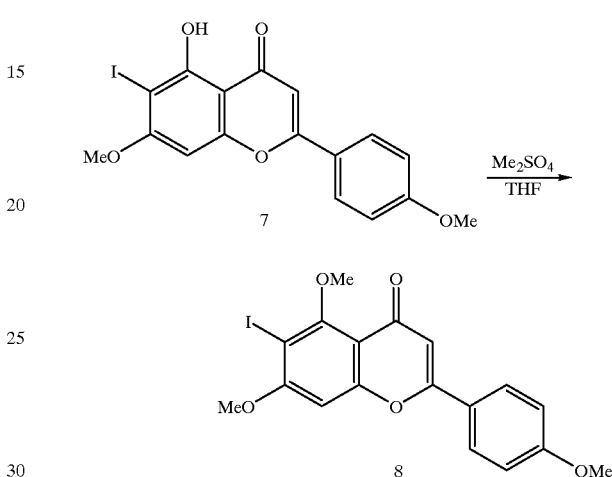

Scheme 3

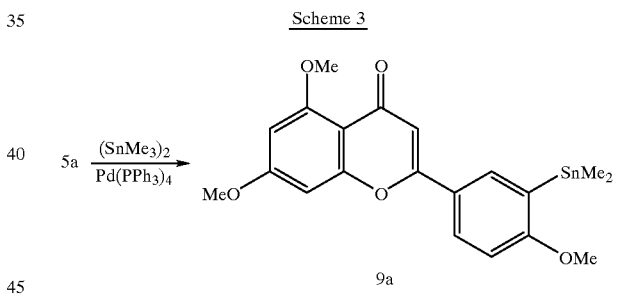

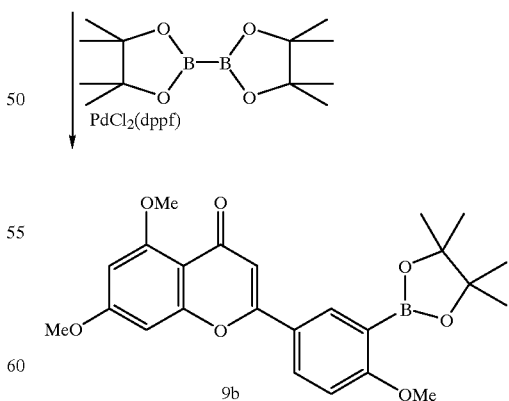

Scheme 4

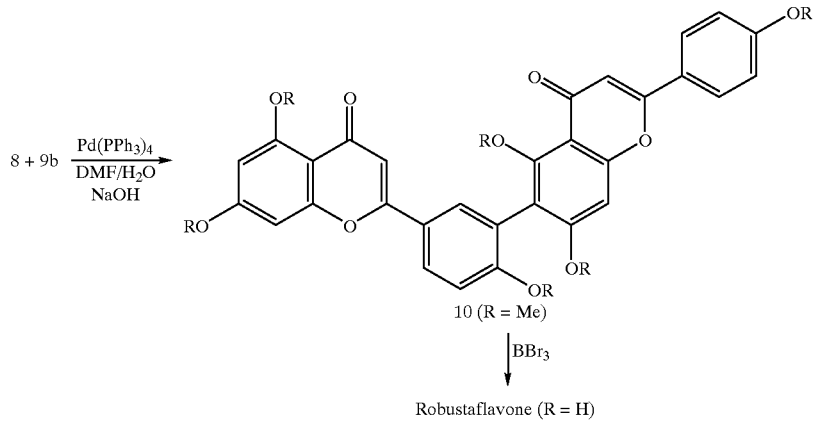

10 (R = Me)

↓ BBr₃

Robustaflavone (R = H)

DETAILED DESCRIPTION OF THE INVENTION

According to the present invention, the total synthesis of robustaflavone was approached via construction of two apigenin derivatives, one substituted in the 6-position and one substituted in the 3'-position, with groups that could be coupled using transition metal-catalyzed cross coupling methodology. The synthesis of apigenin derivatives substituted in the 3'-position is straightforward (Scheme 1), involving esterification of phloroacetophenone dimethyl ether (1) with 3-substituted p-anisoyl chlorides, such as 3-iodo-p-anisoyl chloride (2a). Rearrangement of the resulting ester (3a) to the β-diketone 4a was achieved by heating in pyridine at 100° C. in the presence of powdered KOH. Cyclization of the diketone 4a under acidic conditions provided 3'-iodoapigenin trimethyl ether (5a)[10,23]. This route was also utilized to prepare apigenin trimethyl ether (5b), starting with 1 and p-anisoyl chloride.

The preparation of apigenin derivatives substituted in the 6-position presented a more difficult challenge, as direct electrophilic substitution of apigenin ethers occurs preferentially in the 8-position. An extensive search of the chemical literature yielded only two examples of 6-halogenated apigenin derivatives; the first, described in 1939, reported 6-bromoapigenin trimethyl ether as an intermediate in a total synthesis of apigenin[11]. However, it was later determined that the position of the ring bromination had been incorrectly assigned in the original report, and that the actual intermediate was 8-bromoapigenin trimethyl ether[12]. A second route described the iodination of apigenin 7,4'-dimethyl ether with iodine in an iodic acid solution, which provided a mixture of the 6-iodo and 8-iodo derivatives, in a 1:4 ratio[13]. The desired 6-iodinated derivative was reportedly purified by fractional recrystallization, but in very poor yield.

The desired 6-iodinated species was prepared in excellent yield with almost exclusive regioselectivity by exploiting the ortho-directing capabilities of thallium(I) salts in the iodination of phenols[14] (Scheme 2). Selective demethylation of apigenin trimethyl ether (5b) in the 5-position may be accomplished with boron tribromide in an amount generally ranging between about 0.9 equiv and about 3.0 equiv, preferably about 1.1 equiv boron tribromide, to afford apigenin 7,4'-dimethyl ether (6). The reaction is generally carried out a temperature ranging between about −40° C. and about 50° C., preferably about 25° C., for a time period ranging between about 0.5 h and about 24 h, preferably about 5 h, in the presence of a suitable solvent such as methylene chloride, chloroform, benzene and toluene, preferably methylene chloride, until a thick precipitate is formed. The precipitate is then collected and recrystallized in a suitable solvent such as ethanol, methanol, ethyl acetate/hexane, preferably ethanol. If desired, other boron compounds such as boron trichloride may be used in place of boron tribromide[29].

Thereafter, iodination of 6 is performed with elemental iodine in an amount ranging from about 0.8 equiv to about 1.5 equiv, preferably about 1.0 equiv $I_2$, in the presence of a thallium(I) salt such as thallium(I) acetate, thallium(I) chloride and thallium(I) bromide, preferably thallium(I) acetate, in an amount ranging from about 0.8 equiv and about 1.5 equiv, preferably about 1.2 equiv thallium(I) salt, In a suitable solvent, e.g., $CH_2Cl_2$, to provide 6-iodoapigenin 7,4'-dimethyl ether (7), in excellent yields, containing only trace amounts (less than 1% determined by $^1H$ NMR) of the 8-iodinated species. Methylation of 7 with dimethyl sulfate in an amount ranging between about 1.0 equiv and about 10.0 equiv, preferably about 2.5 equiv, affords the desired 6-iodoapigenin trimethyl ether (8). If desired, other suitable methylating agents such as iodomethane may be used in place of dimethyl sulfate.

Formation of biaryl systems is efficiently achieved via the palladium-catalyzed cross-coupling of aryl halides and aryl boronic acids (Suzuki coupling)[8] or aryl halides and aryl stannanes (Stille coupling)[15], either of which could be applied to the synthesis of robustaflavone from the iodinated species 5a or 8. Conceivably, the iodide of either of these derivatives could be converted to a boronic acid or a stannane, and then cross-coupled with the other iodide to afford robustaflavone hexamethyl ether.

In a related example, derivatives of the biflavanoid amentoflavone were synthesized using the palladium-catalyzed cross-coupling of apigenin ethers bearing a boronic acid in the 8-position with apigenin ethers having an iodide in the 3'-position, in very good yields[9]. The apigenin-8-boronic acids were synthesized from the 8-iodinated derivatives via halogen-lithium exchange, followed by quenching with trimethylborate and aqueous workup. Attempted conversion of the 3'-iodide 5a via halogen-lithium exchange followed by trimethylborate quench were unsuccessful in our hands, as for others[9]. Additionally, our attempt to prepare the corresponding apigenin 6-boronic acid derivative from 8 using this technique were also unsuccessful, in contrast to the reported[9] simple conversion of the 8-iodinated isomer to its corresponding boronic acid.

Milder general methods for the preparation of both stannanes[16] and boronic acids[17] have been described, using the palladium-catalyzed exchange of aryl halides with nucleophilic distannane and diboron reagents, respectively. These methods were applied to compound 5a to afford both the corresponding stannane derivative 9a and boronate 9b, illustrated in Scheme 3. Treatment of 5a with commercially available hexamethylditin in an amount ranging between about 1.0 equiv and about 3.0 equiv, preferably about 2.0 equiv, in the presence of a palladium(0) catalyst[30] suitable for cross-coupling reactions such as $(Ph_3P)_4Pd$, $PdCl_2$(dppf), $PdCl_2$ and $PdCl_2(PPh_3)_2$, preferably $(Ph_3P)_4Pd$, in an amount ranging between about 0.05 equiv and about 0.2 equiv, preferably about 0.1 equiv, in suitable solvent such as toluene, benzene, dioxane and THF, preferably toluene at reflux, affords the trimethylstannane 9a. Generally, the reaction temperature ranges between about 65° C. and about 120° C., preferably about 110° C. If desired, any suitable hexaalkylditin may be used in place of hexamethylditin.

Similarly, treatment of 5a with bis(pinacolato)diboron in an amount ranging between about 1.0 equiv and about 3.0 equiv, preferably about 1.3 equiv, in the presence of catalytic $PdCl_2$(dppf), $Pd(PPh_3)_4$, $PdCl_2$ and $PdCl_2(PPh_3)_2$, preferably $PdCl_2$(dppf), in an amount ranging between about 0.01 equiv and about 0.2 equiv, preferably about 0.13 equiv, and excess $K_2CO_3$ in a suitable solvent such as DMF, DMSO, dioxane or THF, preferably DMF, at a temperature ranging between about 25° C. and about 100° C., preferably about 85° C., provided boronate ester 9b in 64% yield. Bis(pinacolato)diboron was prepared via treatment of tetrakis(trimethylamino) diboron[18] with pinacol as previously described[19], and is commercially available. If desired, pinacolborane[31] or any other suitable nucleophilic source of boron may be used in place of bis(pinacolato)diboron. In addition, $NaHCO_3$, $KHCO_3$ or NaOAc may be used in place of $K_2CO_3$.

Attempted Stille coupling of 9a with iodide 8 in a variety of solvents (DMF, toluene, dioxane, THF) using several palladium catalysts [$(Ph_3P)_4Pd$, $Pd(OAc)_2$, $PdCl_2$, $(Ph_3P)_2PdCl_2$] failed to provide any significant formation of robustaflavone hexamethyl ether (10). When using toluene as solvent, a very small amount of 10 could be detected by TLC, by comparison with an authentic standard prepared by methylation of natural robustaflavone with dimethylsulfate[7], but the major product formed in the reaction was apigenin trimethyl ether (5b). It is commonly accepted that transmetallation from tin to palladium represents the rate limiting step in Stille couplings[15]. Thus, because iodide 8 is particularly reactive toward oxidative addition, accelerated by the presence of the two electron-donating ortho-methoxyl groups, reduction of the aryl iodide apparently occurred much faster than transmetallation. However, it is unclear whether 5b was formed exclusively via reduction of the iodide 8, or also by proteodesilylation of 9a. Following the reaction progress by TLC appeared to indicate that the concentration of 8 decreased over time, while that of 9a was unchanged, suggesting that reduction of 8 was the likely source of 5b.

In contrast to Stille coupling, transmetallation from boron to palladium in Suzuki couplings is rapid, and oxidative addition is generally the rate-limiting step[8]. We thus turned to coupling of boronate 9b with aryl iodide 8. Using reported conditions described17 for coupling of pinacol boronate esters with aryl halides ($PdCl_2$(dppf), DMF, KOAc, 80° C.), we observed that, again, the major product formed was apigenin trimethyl ether (5b). Though we anticipated that coupling between 9b and 8 may be sluggish, due to the steric congestion of the biaryl bond being formed, we were comforted to learn that others[20] had successfully prepared biaryl systems containing similar degrees of steric crowding utilizing Suzuki methodology.

Evaluation of a variety of reaction conditions, conducted by changing the solvent, palladium catalyst, and base, identified coupling conditions that afforded the desired robustaflavone hexamethyl ether (10) starting from compounds 8 and 9b. In practicing this invention, compounds 8 and 9b are both present in the reaction mixture at a range between about 1:1 and about 1:3, preferably about 1:2. Conducting the reaction in a suitable solvent such as DMF, DMSO, dioxane or THF, preferably DMF, containing between about 3% (v/v) and about 25% (v/v) $H_2O$, preferably about 10% (v/v) $H_2O$; between about 1 and about 10 equiv, preferably about 4.0 equiv, of base such as NaOH, KOH, $KHCO_3$, $NaHCO_3$, preferably NaOH; and between about 5 mol % and about 20 mol %, preferably about 10 mol % of a palladium catalyst such as $Pd(PPh_3)_4$, $Pd(OAc)_2$, $PdCl_2$, $PdCl_2(PPh_3)_2$, and $PdCl_2$(dppf), preferably $Pd(PPh_3)_4$, affords 10 in 30% yield, with only small amounts of 5b formed as a by-product, and trace amounts of unreacted iodide 8. It was discovered that utilization of NaOH as base resulted in greatly accelerated reaction rates relative to those observed when using $K_2CO_3$, and the Suzuki coupling was generally complete within one hour. Increasing the equivalence of 9b to 1.2 increased the yield of 10 to 35%, and further increasing the stoichiometry of 9b to 2.0 equivalents increased the yield of 10 to 50%. If desired, other solvent systems can be used in place of water-DMF mixtures for the coupling reaction such as DMF alone or DMSO, dioxane or THF alone or as a mixture with water. The desired material, robustaflavone hexamethyl ether (10) was readily purified using silica gel column chromatography and suitable solvent or solvent mixtures such as chloroform/methanol and ethyl acetate/methanol.

Deprotection of 10 was initially attempted using standard mineral acid conditions, such as HBr and HI. In all cases, the use of mineral acids resulted in Wessely-Moser rearrangement[21], and amentoflavone was the major product isolated. Similar results were obtained using aqueous (HBr and HI) or anhydrous (HBr in HOAc) conditions. Complete demethylation of 10 was achieved by treatment with between about 8 and about 15 equiv $BBr_3$, preferably 12 equivalents $BBr_3$, in a suitable solvent, e.g., $CHCl_3$ at reflux, at a temperature ranging between about 25° C. and about 80° C., preferably about 60–62° C. If desired, $BCl_3$ may be used in place of $BBr_3$. Attempts to deprotect using amounts of $BBr_3$ less than 8 equivalents or at temperatures lower than 50° C., did not achieve complete demethylation, and the resulting products contained significant quantities of partially demethylated materials. Following demethylation, crude robustaflavone was obtained in 88.9% yield. Column chromatography through silica gel (toluene/pyridine/formic acid, 20:10:1) afforded robustaflavone in 30% yield.

The synthesis of robustaflavone analogues can be approached using the Suzuki cross-coupling methodology that was developed during the total synthesis of robustaflavone, or the Stille coupling methods. Either of the aryl iodides 5b or 8 could be cross-coupled with an aryl- or alkylboronic acid derivative, or with an aryl- or alkylstannane, to afford 3'- and 6-substituted apigenin derivatives, respectively, which effectively represent robustaflavone intermediates or analogues. To serve as an example, 6-(2-methoxyphenyl) apigenin trimethyl ether 11 was efficiently synthesized via the Suzuki coupling of 8 with commercial 2-methoxyphenylboronic acid as illustrated in Scheme 5 and described in Example 2.

For the formation of robustaflavone analogues, any number of aryl- or alkyl boronic acids, available either from commercial vendors or prepared from aryl halides using standard halogen-lithium exchange/borate quench, could be cross-coupled with iodides 8 or 5b (Scheme 6), using the general conditions described for the synthesis of 11. Following the cross-coupling step, removal of the protective groups, such as described for the conversion of 10 to robustaflavone, will provide the final robustaflavone analogues. The reagents "R-X" embody any appropriate reagent which will cross-couple with aryl iodides, including aryl- and alkylboronic acids[26], aryl- and alkylstannanes[27], and primary or secondary aliphatic or aromatic amines[28]. Suitable, but not limiting, examples of aryl include phenyl and phenyl substituted with one or more alkyl groups, preferably $C_1$–$C_6$ groups, which may be further substituted with one or more halogens, alkoxy groups, and amino groups. Suitable, but not limiting, examples of primary or secondary aliphatic or aromatic amines include, without limitation, n-propylamine, pyrrolidine and aniline.

Alternatively, boronic acid derivative 9b could be cross-coupled with aryl halides, to afford 3'-substituted apigenin derivatives, which would effectively represent robustaflavone analogues. This route would offer the advantage that many organic aryl halides representing a wide variety of structural diversity are commercially available. Additionally, iodide 8 could be converted to its corresponding 6-boronic acid derivative (12) using the same general route illustrated for the synthesis of 9b in Scheme 3. At that point, apigenin derivatives bearing boronic acid moieties in both the 3'- and 6-positions would be available, and allow the rapid construction of analogues via cross-coupling with any variety of organic aryl halide, including but not limited to substituted halogenated benzenes such as iodonitrobenzene and bromoanisole; halogenated heteroaromatics such as bromopyridine, bromothiophene and bromofuran; and halogenated polycyclic aromatics such as bromonaphthalene, bromoanthraquinone and bromoanthracene and heteroaromatics such as bromoindole, bromoquinoline and bromobenzofuran (Scheme 7), as well as aryl- and vinyltriflates.

The generation of robustaflavone derivatives is not restricted to the use of apigenin derivatives protected as methyl ethers. An ordinary skilled artisan would appreciate that the phenol moieties of apigenin could be protected with other alkyl ether groups, including but not limited to isopropyl and benzyl, which could offer simpler deprotection conditions. Alternatively, the phenol moieties could be protected as esters of appropriate carboxylic acids such as acetic acid and benzoic acid.

Scheme 5

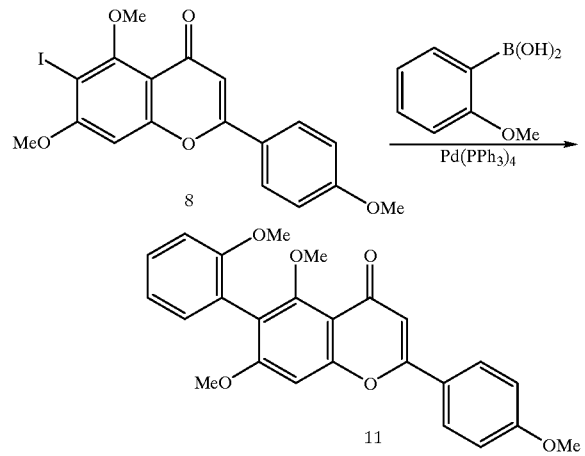

Scheme 6

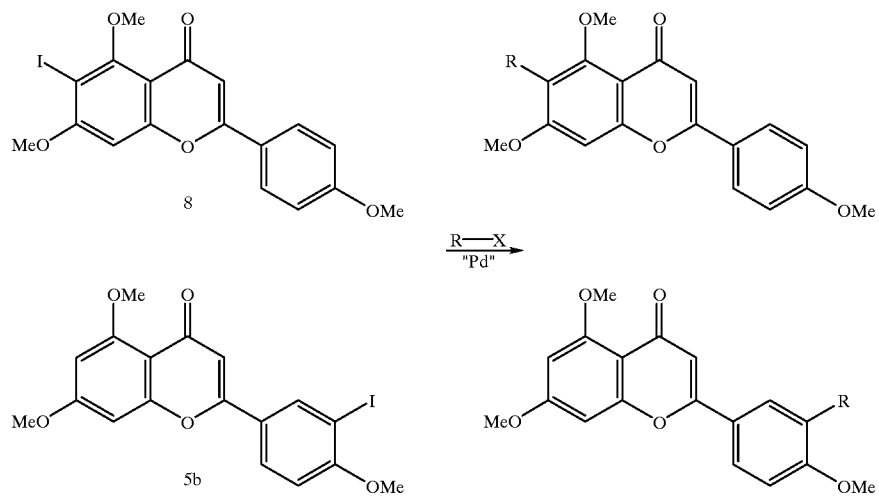

Scheme 7

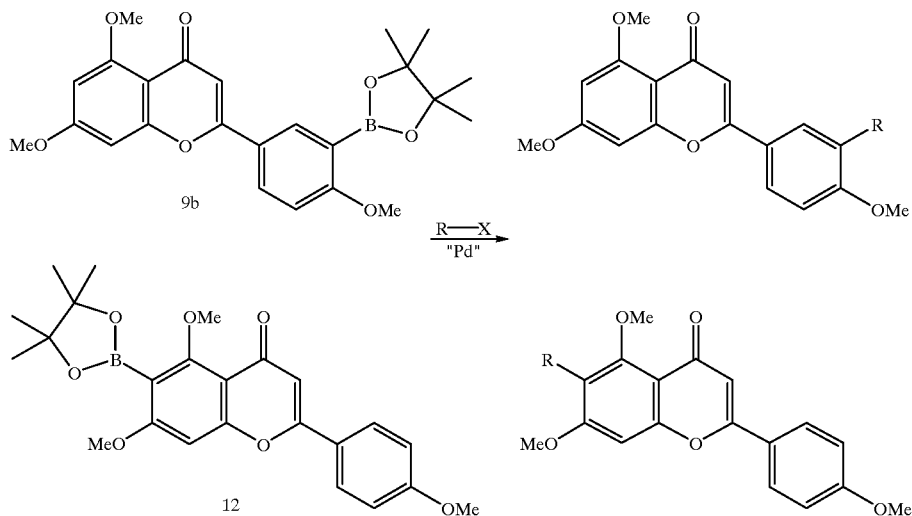

The following Examples are illustrative of the present invention and do not serve to limit the scope of the invention as claimed. Example 1 describes preparation of robustaflavone by the method of the present invention. Example 2 describes preparation of 6-(2-methoxyphenyl) apigenin trimethyl ether, a product produced by the Suzuki coupling of 8 with a commercial 2-methoxyphenylboronic acid.

EXPERIMENT NO. 1

TOTAL SYNTHESIS OF ROBUSTAFLAVONE

General Experimental. 300 MHz $^1$H NMR spectra were recorded on a Varian Gemini 2000 spectrometer. Chemical shifts are reported on the δ scale downfield from tetramethylsilane. EI mass spectra were obtained with a Finnigan MAT 90 mass spectrometer, and APCI mass spectra were recorded with a Finnigan MAT LCQ mass spectrometer. Infrared spectra were recorded with either a Midac M series or a Perkin Elmer Spectra 1000 FTIR spectrophotometer. Elemental analyses were obtained from Midwest Microlab, Indianapolis, Ind. Melting points were determined with a Mel-Temp melting point apparatus and are corrected. Column chromatography was conducted with EM Science silica gel 60 (70–230 mesh) with indicated eluents. Analytical thin layer chromatography was performed with silica gel 60 $F_{254}$ precoated glass-backed plates (250 μm) with indicated eluents. Bis(pinacolato)diboron was prepared from tetrakis(dimethylamino)diboron[18] as previously described[19]. All other reagents and solvents were purchased from commercial sources and used without further purification.

2,4-Dimethoxy-6-hydroxyacetophenone (1). To a solution of phloroacetophenone hydrate (20.5 g, 110 mmol) and $K_2CO_3$ (22.1 g, 160 mmol) in 150 mL acetone was added dimethylsulfate (27.7 g, 220 mmol) slowly over 30 min with mechanical stirring. The solution was heated at reflux overnight, then poured into 500 mL $H_2O$, which produced a white solid. The material was collected on a Büchner funnel, rinsed with 1 L $H_2O$ and air dried. Recrystallization from 80 mL of 90% MeOH afforded white needles (16.1 g, 74.4%); mp 79° C. (lit.[10] mp 82–83° C.); $^1$H NMR (CDCl$_3$) δ 2.61 (s, 3 H), 3.82 (s, 3 H), 3.86 (s, 3 H), 5.92 (d, 1 H, J=2.4 Hz), 6.06 (d, 1 H, J=2.4 Hz), 7.26 (s, 1 H), 14.03 (s, 1 H).

3-Iodo-p-anisic Acid. To a mechanically stirred suspension of p-anisic acid (59.90 g, 394 mmol) and iodine (100.0 g, 394 mmol) in a mixture of 325 mL glacial acetic acid and 60 g conc $H_2SO_4$, heated to 45° C. with a water bath, was added dropwise a solution of 40 g conc $HNO_3$ in 60 mL HOAc at such a rate that the temperature was maintained between 40–50° C. (ca. 90 min). After addition, the mixture was stirred for 30 min at 50° C., then diluted with 400 mL $H_2O$, which produced a pink solid. The material was collected on a Büchner funnel, rinsed with 1 L 10% $Na_2S_2O_4$ and 1 L $H_2O$, then air dried. Recrystallization from 700 mL pyridine/MeOH (1:1) provided colorless plates. The crystals were collected on a Büchner funnel, rinsed with 500 mL MeOH, then allowed to air dry. After drying under high vacuum overnight, 71.4 g (65.2%) of the desired product was obtained; mp 243–244° C. (lit.[10] mp 238° C.); $^1$H NMR (DMSO-d$_6$) δ 3.91 (s, 3 H), 7.00 (d, 1 H, J=8.7 Hz), 7.95 (dd, 1 H, J=8.7, 1.8 Hz), 8.27 (d, 1 H, J=1.8 Hz), 12.89 (br s, 1 H).

3-Iodo-p-anisoyl chloride (2a). To a suspension of PCl$_5$ (33.0 g, 158 mmol) in 30 mL CHCl$_3$ was added, with magnetic stirring, 3-iodo-p-anisic acid (40.0 g, 144 mmol) in small portions. The solution was heated at reflux for b 1h under a gentle nitrogen sweep, during which time the solution became homogenous. The solvent was evaporated under reduced pressure, then the residue was distilled under high vacuum. The fraction distilling at 152–156° C. (5 mm Hg; lit.[10] bp 183–185° C., 12–13 mm Hg) was collected, which rapidly solidified as a pink solid. Recrystallization from 200 mL hexane/CH$_2$Cl$_2$ afforded the desired product as white needles (36.4 g, 85.5%); mp 58° C.; $^1$H NMR (CDCl$_3$) δ 3.99 (s, 3 H), 6.88 (d, 1 H, J=8.7 Hz), 8.13 (dd, 1 H, J=8.7, 2.4 Hz), 8.52 (d, 1 H, J=2.4 Hz); EI-MS m/z 296 (M$^+$, 42), 261 (100).

4,6-Dimethoxy-2-(3'-iodo-4'-methoxybenzoyloxy)acetophenone (3a). To a solution of 1 (5.00 g, 25.5 mmol) in 15 mL pyridine was added 2a (9.08 g, 30.6 mmol), and the solution heated to 100° C. in an oil bath with magnetic stirring for 10 min. The solution was cooled to room temperature, then diluted with 20 mL MeOH. The solution was cooled in an ice bath and, following scratching with a glass rod, colorless needles formed. The crystals were collected on a Büchner funnel, rinsed with cold McOH and air dried to provide 10.1 g (86.4%) of the desired product; mp 146° C. (lit.[10] mp 158° C.; $^1$H NMR (CDCl$_3$) δ 2.47 (s, 3 H), 3.83 (s, 3 H), 3.87 (s, 3 H), 3.96 (s, 3 H), 6.34 (d, 1 H, J=2.1 Hz), 6.41 (d, 1 H, J=2.1 Hz), 6.87 (d, 1H, J=8.7 Hz), 8.12 (dd, 1H, J=8.7, 2.1 Hz), 8.55 (d, 1 H, J=2.1 Hz); EI-MS m/z 456 (M$^+$, 41), 261 (100).

1-(3'-Iodo-4'-methoxyphenyl)-3-(2"-hydroxy-3",6"-dimethoxyphenyl)-1,3-propanedione (4a). To a suspension of 3a (9.12 g, 20.0 mmol) in 20 mL pyridine was added 2.80 g (50 mmol) powdered KOH, and the solution heated to 100° C. with magnetic stirring in an oil bath for 10 min. The solution was cooled to room temperature and treated with 10 mL HOAc, which produced a yellow paste. Addition of 20 mL MeOH and cooling in an ice bath afforded a yellow powder, which was collected on a Büchner funnel, rinsed with 100 mL MeOH and air dried to provide 5.68 g (62.3%) of the desired product; mp 170–171° C. (lit.[10] mp 168° C.); $^1$H NMR (CDC$_3$) δ 3.51 (s, 3 H), 3.82 (s, 3 H), 3.97 (s, 3 H), 4.48 (s, 2 H), 5.85 (d, 1 H, J=2.1 Hz), 6.09 (d, 1 H, J=2.1 Hz), 6.89 (d, 1 H, J=8.7 Hz), 7.96 (dd, 1 H, J=8.7, 2.1 Hz), 8.40 (d, 1 H, J=2.1 Hz), 13.68 (s, 1H); EI-MS m/z 456 (M$^+$, 70), 181 (100).

3'-Iodo-5,7,4'-trimethoxyflavone (5a). To a magnetically stirred solution of 4a (5.00 g, 11.0 mmol) in 60 mL HOAc at 100° C. (water bath) was added 10 mL of 20% H$_2$SO$_4$/HOAc. After stirring at 100° C. for 10 min, the solution was poured into 250 mL H$_2$O, which produced a white precipitate. The solid was collected on a Büchner funnel, rinsed with 500 mL H$_2$O and air dried. Recrystallization from 150 mL dioxane produced white needles (2.83 g, 58.9%). Evaporation of the mother liquor and recrystallization afforded an additional 1.35 g (total yield 4.18 g, 87.0%); mp 209–210° C. (lit.[10] mp 223° C.); $^1$H NMR (DMSO-d$_6$) δ 3.83 (s, 3 H), 3.91 (s, 3 H), 3.92 (s, 3 H), 6.50 (d, 1 H, J=2.1 Hz), 6.73 (s, 1 H), 6.91 (d, 1 H, J=2.1 Hz), 7.14 (d, 1 H, J=8.7 Hz), 8.06 (dd, 1 H, J=8.7, 2.4 Hz), 8.41 (d, 1 H, J=2.4 Hz); EI-MS m/z 438 (M$^+$, 100).

4,6-Dimethoxy-2-(4'-methoxybenzoyloxy)acetophenone (3b). To a solution of 1 (20.0 g, 102 mmol) in 60 mL pyridine was added 20.9 g (122 mmol)p-anisoyl chloride (2b), and the solution heated at 100° C. for 10 min with magnetic stirring in an oil bath. The solution was cooled to room temperature, then diluted first with 50 mL EtOH followed by 50 mL H$_2$O. The mixture was cooled to 0° C. in an ice bath which, after scratching with a glass rod, produced shiny white plates. The crystals were collected on a Büchner funnel, rinsed with cold 50% EtOH and air dried to afford 27.4 g (81.4%) of desired product; mp 97–98° C. (lit.[23] mp 115–116° C.); $^1$H NMR (CDCl$_3$) δ 2.46 (s, 3 H), 3.82 (s, 3 H), 3.86 (s, 3 H), 3.88 (s, 3 H), 6.37 (d, 1 H, J$_{AB}$=2.1 Hz), 6.39 (d, 1 H, J$_{AB}$=2.1 Hz), 6.96 (d, 2 H, J=8.9 Hz), 8.09 (d, 2 H, J=8.9 Hz); EI-MS m/z 330 (M$^+$, 23), 135 (100). Anal. calcd for C$_{18}$H$_{18}$O$_6$: C, 65.45; H, 5.49. Found: C, 65.55; H, 5.57.

1-(4'-Methoxyphenyl)-3-(2"-hydroxy-3",6"-dimethoxyphenyl)-1,3-propanedione (4b). To a solution of 3b (30.0 g, 90.8 mmol) in 120 mL pyridine was added 12.7 g (153 mmol) powdered KOH, and the solution heated to 100° C. in an oil bath with magnetic stirring for 10 min. The mixture was cooled to room temperature, then treated with 50 mL glacial acetic acid, which produced a thick yellow paste. The mixture was diluted with 100 mL EtOH, which afforded a homogenous solution, followed by 100 mL H$_2$O. Upon cooling to 0° C., the product crystallized as yellow prisms. The crystals were collected on a Büchner funnel, rinsed with cold 50% EtOH and air dried to provide 20.72 g (69.1%) of desired product; mp 132–133° C. (lit.[23] mp 147–149° C.); $^1$H NMR (CDCl$_3$) δ 3.48 (s, 3 H), 3.81 (s, 3 H), 3.89 (s, 3 H), 4.51 (s, 2 H), 5.83 (d, 1 H, J=2.4 Hz), 6.09 (s, 1 H, J=2.4 Hz), 6.97 (d, 2 H, J=9.1 Hz), 7.94 (d, 2 H, J=9.1 Hz), 13.74 (s, 1 H); FTIR (KBr) 3071, 1724, 1584, 1182, 1138 cm$^{-1}$; EI-MS m/z 330 (M$^+$, 46), 135 (100). Anal. calcd for C$_{18}$H$_{18}$O$_6$: C, 65.45; H, 5.49. Found: C, 65.38; H, 5.54. The $^1$H NMR spectra also indicated the presence of enol tautomers.

5,7,4'-Trimethoxyflavone (apigenin trimethyl ether, 5b). A suspension of 4b (18.6 g, 56.4 mmol) in 200 mL glacial acetic acid was heated to 100° C. with magnetic stirring in an oil bath. To this suspension was added 40 mL of 20% H$_2$SO$_4$ in acetic acid, and the mixture stirred at 100° C. for 10 min. The mixture was poured into 1 L H$_2$O, which produced a pale-yellow gelatinous solid. The solid was collected on a Büchner funnel, allowed to partially dry by drawing air through the funnel, and then partitioned between 600 mL each of CHCl$_3$ and H$_2$O. The organic layer was separated and washed with 600 mL each of 5% NaHCO$_3$ and saturated brine, dried over magnesium sulfate, filtered and evaporated to afford a light yellow solid. Recrystallization from 300 mL acetone provided white needles (12.45 g, 70.8%); mp 159° C. (lit.[24] mp 156° C.); $^1$H NMR (DMSO-d$_6$) δ 3.83 (s, 3 H), 3.85 (s, 3 H), 3.90 (s, 3 H), 6.50 (d, 1 H, J=2.1 Hz), 6.67 (s, 1 H), 6.84 (d, 1 H, J=2.1 Hz), 7.09 (d, 2 H, J=8.9 Hz), 7.99 (d, 2 H, J=8.9 Hz; FTIR (KBr) 1644, 1348, 1256, 1121, 831 cm$^{-1}$; EI-MS m/z 312 (M$^+$, 100). Anal. calcd for C$_{18}$H$_{16}$O$_5$: C, 69.22; H, 5.16. Found: C, 69.35; H, 5.32.

7,4'-Dimethoxy-5-hydroxyflavone (6). To a solution of 5b (10.0 g, 32.1 mmol) in 200 mL anhydrous CH$_2$Cl$_2$ was added dropwise a 1 M solution of BBr$_3$ (35.3 mL, 35.3 mmol) over 15 min at room temperature with magnetic stirring. A thick yellow precipitate formed rapidly during the addition. After stirring 5 h, the reaction was quenched by adding 200 mL EtOH, and the solvent was then evaporated in vacuo. The yellow residue was triturated with 300 mL boiling 50% EtOH. After cooling to room temperature, the yellow solid was collected on a Büchner funnel, rinsed with 500 mL 50% EtOH and air dried. Recrystallization from 1.5 L EtOH provided 8.16 g (85.4%) of the title product as fine, pale-yellow needles; mp 176–177° C. (lit.[25] mp 174–175° C.); $^1$H NMR (CDCl$_3$) δ 3.88 (s, 3 H), 3.89 (s, 3 H), 6.36 (d, 1 H, J=2.1 Hz), 6.48 (d, 1 H, J=2.1 Hz), 6.57 (s, 1 H), 7.01 (d, 2 H, J$_{AB}$=9.0 Hz), 7.84 (d, 2 H, J$_{AB}$=9.0 Hz), 12.81 (s, 1 H); EI-MS m/z 298 (M$^+$, 100). Anal. calcd for C$_{17}$H$_{14}$O$_5$: C, 68.45; H, 4.73. Found: C, 68.25; H, 4.77.

7,4'-Dimethoxy-5-hydroxy-6-iodoflavone (7). To a solution of 6 (2.98 g, 10.0 mmol) in 300 mL CH$_2$Cl$_2$ was added thallium(I) acetate (3.16 g, 10.2 mmol). With magnetic stirring, a solution of iodine (2.54 g, 10.0 mmol) in 200 mL CH$_2$Cl$_2$ was added dropwise over 1 h. During the addition, a fine suspension of thallium salts precipitated. The solution was stirred at room temperature overnight, then filtered through a bed of celite to remove the precipitated salts. The filtrate was extracted sequentially with 500 mL each of 5% NaHCO$_3$, 10% Na$_2$S$_2$O$_4$, and saturated brine, then dried over magnesium sulfate and filtered. Evaporation in vacuo provided an orange solid. Recrystallization from 300 mL CHCl$_3$/EtOH (1:2) afforded fine yellow needles (3.10 g, 73.1%); mp 227–228° C. (lit.[13] mp 205–207° C.); $^1$H NMR (CDCl$_3$) δ 3.90 (s, 3 H), 4.00 (s, 3 H), 6.54 (s, 1 H), 6.64 (s, 1 H), 7.02 (d, 2 H, J=9.0 Hz), 7.85 (d, 2 H, J=9.0 Hz), 13.84 (s, 1 H); $^{13}$C NMR (75 MHz, CDCl$_3$) δ 181.7, 164.4, 163.5, 162.9, 161.3, 158.3, 128.2, 123.3, 114.6, 104.4, 104.3, 90.5, 90.4, 56.8, 55.5; EI-MS m/z 424 (M+, 100). Anal. calcd for $C_{17}H_{13}IO_5$: C, 48.14; H, 3.09. Found: C, 48.30; H, 3.11.

6-Iodo-5,7,4'-trimethoxyflavone (8). To a solution of 7 (3.00 g, 7.08 mmol) and $K_2CO_3$ (1.47 g, 10.6 mmol) in 150 mL THF was added dimethylsulfate (1.07 g, 8.49 mmol) and the solution heated at reflux overnight. The solvent was evaporated and the residue partitioned between 50 mL each of $CHCl_3$ and $H_2O$. The organic phase was separated and washed with saturated brine, dried over magnesium sulfate, filtered and evaporated to provide a yellow solid. Recrystallization from $CHCl_3$/EtOH (1:2, 150 mL) afforded pale-yellow needles. Column chromatography of the evaporated mother liquor (100 g silica gel, 2% MeOH/$CH_2Cl_2$) afforded an additional 720 mg of desired product (total yield 2.21 g, 71.3%); mp 204° C. (lit.[13] mp 191–194° C.); $^1$H NMR ($CDCl_3$) δ 3.89 (s, 3 H), 3.94 (s, 3 H), 4.01 (s, 3 H), 6.62 (s, 1 H), 6.78 (s, 1 H), 7.01 (d, 2 H, J=9.1 Hz), 7.83 (d, 2 H, J=9.1 Hz); EI-MS in/z 438 (M+, 65), 311 (100). Anal. calcd for $C_{18}H_{15}IO_5$: C, 49.34; H, 3.45. Found: C, 48.58; H, 3.21.

5,7-4'-Trimethoxy-3'-(trimethylstannyl)flavone (9a). To a solution of 5a (438 mg, 1.00 mmol) in 30 mL toluene was added Pd(Ph$_3$P)$_4$ (150 mg, 0.13 mmol) and hexamethylditin (655 mg, 2.00 mmol), and the solution heated to reflux under $N_2$ for 16 h. The solution was filtered and the solvent evaporated in vacuo. The residue was dissolved in 75 mL $CHCl_3$, washed with 75 mL saturated brine, dried over magnesium sulfate, filtered and evaporated to provide a white crystalline solid. The solid was triturated with 10 mL EtOH, collected on a Buchner funnel, rinsed with fresh EtOH and air dried (270 mg, 56.8%). An analytical sample was obtained via recrystallization from EtOH, which produced fine colorless needles; mp 154° C.; $^1$H NMR (DMSO-d$_6$) δ 0.31 (s, 9 H), 3.83 (s, 3 H), 3.85 (s, 3 H), 3.91 (s, 3 H), 6.51 (d, 1 H, J=2.4 Hz), 6.65 (s, 1 H), 6.82 (d, 1 H, J=2.4 Hz), 7.08 (d, 1 H, J=8.7 Hz), 7.86 (d, 1 H, J=2.4 Hz), 8.01 (dd, 1 H, J=8.7, 2.4 Hz); $^{13}$C NMR (75 MHz, $CDCl_3$) δ 177.9, 166.5, 164.0, 161.4, 161.0, 160.1, 134.3, 131.7, 128.6, 124.1, 109.1, 107.7, 96.0, 92.9, 56.4, 55.7, 55.5; EI-MS m/z 476 (M+, 64), 461 (100). Anal. calcd for $C_{21}H_{24}O_5Sn$: C, 53.09; H, 5.09. Found: C, 52.74; H, 5.01.

Pinacol 5,7-4'-trimethoxyflavone-3'-boronate (9b). A solution of 5a (2.00 g, 4.56 mmol), bis(pinacolato)diboron (1.50 g, 5.93 mmol), KOAc (1.79 g, 18.24 mmol) and PdCl$_2$(dppf) (372 mg, 0.456 mmol) in 60 mL DMF was stirred at 80° C. overnight. The reaction mixture was filtered, diluted with 200 mL EtOAc, then washed with $H_2O$ (3×) and brine. After drying over sodium sulfate, the solvent was evaporated. The product was chromatographed over silica gel (EtOAc/MeOH, 96:4) to afford 1.21 g (60.5%) of the desired product as a gray solid. The material could be recrystallized from $CH_2Cl_2$/EtOAc, as pale gray needles; mp 218–220° C.; $^1$H NMR ($CDCl_3$) δ 1.39 (s, 12 H), 3.91 (s, 3 H), 3.92 (s, 3 H), 3.96 (s, 3 H), 6.38 (d, 1 H, J=2.2 Hz), 6.60 (d, 1 H, J=2.2 Hz), 6.66 (s, 1 H), 6.96 (d, 1 H, J=8.9 Hz), 7.96 (dd, 1 H, J=8.9, 2.4 Hz), 8.18 (d, 1 H, J=2.4 Hz); $^{13}$C NMR ($CDCl_3$) δ 177.9, 166.6, 164.0, 161.0, 160.9, 160.0, 134.9, 130.4, 123.3, 114.4, 110.6, 109.3, 107.8, 96.0, 93.0, 83.9, 56.4, 55.9, 55.7, 24.7; FTIR (KBr) 1645, 1602, 1330, 1148 cm$^{-1}$; APCI-MS m/z 439 (MH+, 100). Anal. calcd for $C_{24}H_{27}BO_7$. ½ $H_2O$: C, 64.45; H, 6.31. Found: C, 64.17; H, 6.05.

Robustaflavone hexamethyl ether (10). To a solution of 8 (25.0 mg, 0.057 mmol) and 9a (50.0 mg, 0.114 mmol) in DMF/$H_2O$ (9:1) which had been deoxygenated for 15 min by bubbling $N_2$, was added NaOH (9.1 mg, 0.23 mmol) and Pd(PPh$_3$)$_4$ (6.6 mg, 0.0057 mmol), and the reaction stirred at 80° C. for 2 h. The solution was diluted with $CH_2Cl_2$, then extracted with $H_2O$ and saturated brine. The organic layer was dried over magnesium sulfate, filtered and evaporated in vacuo. Column chromatography (silica gel, $CH_2Cl_2$/MeOH, 96:4) afforded the desired product 10 (17.7 mg, 50%), identical with an authentic sample prepared via methylation of robustaflavone[7]: mp 296–297° C. (lit.[7] mp 303–305° C.) $^1$H NMR ($CDCl_3$) δ 3.62 (s, 3 H), 3.85 (s, 3 H), 3.87 (s, 3 H), 3.91 (s, 6 H), 3.96 (s, 3 H), 6.37 (d, 1 H, J=2.1 Hz), 6.60 (d, 1 H, J=2.4 Hz), 6.69 (s, 1 H), 6.74 (s, 1 H), 6.89 (s, 1 H), 7.04 (d, 2 H, J=9.0 Hz), 7.10 (d, 1 H, J=8.7 Hz), 7.81 (d, 1 H, J=2.4 Hz), 7.89 (d, 2 H, J=9.0 Hz), 7.89 (dt, 1 H, J=2.1, 8.7 Hz). Anal. calcd for $C_{36}H_{30}O_{10}$.½ $H_2O$: C, 68.46; H, 4.91. Found: C, 68.28; H, 5.19.

Robustaflavone. To a solution of 10 (75.0 mg, 0.12 mmol) in 10 mL dry $CHC_3$ was added BBr$_3$ (1.0 M in $CH_2Cl_2$, 1.45 mL, 1.45 mmol), and the resulting yellow slurry was stirred at reflux overnight. The reaction mixture was cooled to room temperature, quenched by the careful addition of MeOH, and evaporated in vacuo. The resulting orange solid was triturated with MeOH, the solvent again evaporated in vacuo, and the solid was partitioned between EtOAc and 1 M NaOH. The organic layer was discarded, and the aqueous layer was extracted with EtOAc. After cooling to 0° C., the aqueous layer was carefully acidified to pH 3.0 by the dropwise addition of 3 M HCl. The resulting yellow precipitate was collected by vacuum filtration, rinsed with water and air dried (38.7 mg). The crude material was chromatographed through silica gel, eluting with a mixture of toluene/pyridine/formic acid (20:10:1). Appropriate fractions were combined and evaporated to afford 19.4 mg (30.0%) robustaflavone. An analytical sample was obtained via recrystallization from pyridine/$H_2O$ (1:1); mp 370–372° C., dec. (lit.[1] mp 350–352° C.). Spectral data of synthetic robustaflavone was identical to that recently reported1 for the natural product isolated from Rhus succedanea. Anal. calcd for $C_{30}H_{18}O_{10}$.1.25 $H_2O$: C, 64.23; H, 3.68. Found: C, 64.17; H, 3.68.

EXAMPLE NO. 2

6-(2-Methoxyphenyl) Apigenin Trimethyl Ether (11).

To a solution of 8 (25 mg, 0.057 mmol) and 2-methoxyphyenylboronic acid (13 mg, 0.086 mmol) in a mixture of DMF/$H_2O$ (9:1) containing 9.1 mg (0.228) NaOH was added Pd (PPh$_3$)$_4$ (6.6mg, 0.0057 mmol). The solution was magnetically stirred for 90 minutes at 80° C. then cooled to room temperature. After diluting with EtOAc, the solution was washed with $H_2O$ and saturated brine, then dried over magnesium sulfate, filtered and concentrated in vacuo. The residue was purified using silica gel column chromatography (EtOAc/hexane, 1:1) to afford 15.8 mg (66.2%) of the anticipated product; $^1$H NMR (CDCL$_3$) 3.60 s, 3 H), 3.76 (s, 3H), 3.84 (s, 3H), 3.90 (s, 3 H), 6.62 (s, 1 H), 6.85 (s, 1 H), 7.03 (m, 4H), 7.20 (dd, 1 H, J=8.0, 1.5 Hz), 7.39 (dt, 1 H, J=7.9, 1.5 Hz), 7.86 (m, 2H); APCI-MS m/z 419 (MH+, 100), 405.

While the fundamental novel features of the invention have been described, it will be understood that various omissions, substitutions and changes in the form and details illustrated may be made by those skilled in the art without departing from the spirit of the invention. It is the intention, therefore, to be limited only as indicated by the scope of the claims.

REFERENCES (1) Lin, Y.-M.; Zembower, D. E.; Flavin, M. T.; Schure, R. M.; Anderson, H. M.; Korba, B. E.; Chen, F.-C. Bioorg. Med. Chem. Lett. 1997, 7, 2325–2328.

(2) Hoofnagle, J. H. N. *Engl. J. Med.* 1990, 323, 337–339.
(3) Aach, R. D. *Ann. Intern. Med.* 1988, 109, 89–91.
(4) Martin, P.; Friedman, L. S. In *Innovations in Antiviral Development and the Detection of Virus Infections*; Block, T. M., Junkind, D., Crowell, R. L., Denison, M., Walsh, L. R., Eds.; Plenum Press: New York, 1992, pp. 111–120.
(5) Maynard, J. E.; Kane, M. A.; Hadler, S. C. *Rev. Infect. Dis.* 1989, 11, S574–S578.
(6) Varshney, A. K.; Rahman, W.; Okigawa, M.; Kawano, N. *Experimentia* 1973, 29, 784–786.
(7) Lin, Y.-M.; Chen, F.-C. *Phytochem.* 1974,13, 1617–1619.
(8) Miyaura, N.; Suzuki, A. *Chem. Rev.* 1995, 95, 2457–2483.
(9) Muller, D.; Fleury, J.-P. *Tetrahedron Lett.* 1991, 32, 2229–2232.
(10) Nakazawa, K. *Chem. Pharm. Bull.* 1962, 10, 1032–1038.
(11) Hutchins, W. A.; Wheeler, T. S. *J. Chem. Soc.* 1939, 91–94.
(12) Chang, C. T.; Chen, T. S.; Chen, F. C. *J. Org. Chem.* 1961, 26, 3142–3143.
(13) Ahmad, S.; Razaq, S. *Pak. J. Sci. Ind. Res.* 1972, 15, 361–362.
(14) Cambie, R. C.; Rutledge, P. S.; Smith-Palmer, T.; Woodgate, P. D. *J. Chem. Soc. Perkin Trans.* I 1976, 1161–1164.
(15) Stille, J. K. *Angew. Chem. Int. Ed. Eng.* 1986, 25, 508–524.
(16) Azizian, H.; Eaborn, C.; Pidcock, A. *J. Organomet. Chem.* 1981, 215, 49–58.
(17) Ishlyama, T.; Murata, M.; Miyaura, N. *J. Org. Chem.* 1995, 60, 7508–7510.
(18) Brotherton, R. J.; McCloskey, A. L.; Petterson, L. L.; Steinberg, H. *J. Am. Chem. Soc.* 1960, 82, 6242–6245.
(19) Nöth, H. Z. *Naturforsch.* 1984, 39b, 1463–1466.
(20) Johnson, M. G.; Foglesong, R. J. *Tetrahedron Lett.* 1997, 38, 7001–7002.
(21) Wessely, F.; Moser, G. H. *Monatsch. Chem.* 1930, 56, 97–105.
(22) Zembower, D. E.; Lin, Y.-M.; Flavin, M. T.; Chen, F.-C.; Korba, B. E. *Antiviral Res.* 1998, in press.
(23) Roy, D.; Khanna, R. N. *Indian J. Chem.* 1980, 19B, 583–586.
(24) Schmid, L.; Waschkau, A. *Monatsch. Chem.* 1928, 49, 83–91.
(25) Dawson, R. M.; Henrick, C. A.; Jefferies, P. R.; Middleton, E. J. *Aust. J. Chem.* 1965, 18, 1871–1875.
(26) Miyaura, N.; Suzuki, A. Palladium-Catalyzed Cross-Coupling Reactions of Organoboron Compounds. *Chem. Rev.* 1995, 95, 2457–2483.
(27) Stille, J. K. The Palladium-Catalyzed Cross-Coupling of Organotin Reagents with Organic Electrophiles, *Angew. Chem. Int. Ed. Eng.* 1986, 25, 508–524.
(28) Marcoux, J.-F.; Wagaw, S.; Buchwald, S. L. Palladium-Catalyzed Amination of Aryl Bromides: Use of Phosphinoether Ligands for the Efficient Coupling of Acyclic Secondary Amines. *J. Org. Chem.* 1997, 62, 1568–1569.
(29) Dean, F. M.; Goodchild, J.; Houghten, L. E.; Martin, J. A.; Morton, R. B.; Parton, B.; Price, A. W.; Samvichien, N. Boron Trichloride as a Selective Demethylating Agent. *Tetrahedron Lett.* 1966, 4153–4159.
(30) For examples of palladium(0) catalysts which catalyze cross-coupling reactions, see Richard Heck "Palladium Reagents in Organic Synthesis," 1985, Academic Press, London.
(31) Murata, M.; Watanabe, S.; Masuda, Y., *J. Org. Chem.* 1997, 62, 6458–6459.

We claim:

1. A method for preparing robustaflavone comprising the steps of:

(a) reacting 6-iodo-5,7,4'-trimethoxyflavone 8 and 5,7-4'-trimethoxy-3'-(trimethylstannyl)flavone 9a in the presence of a palladium compound and a base to produce robustaflavone hexamethyl ether 10; and (b) demethylating robustaflavone hexamethyl ether to produce robustaflavone.

2. The method of claim 1 wherein the palladium compound is a member selected from the group consisting of $Pd(PPh_3)_4$, $Pd(OAc)_2$, $PdCl_2$, $PdCl_2(PPh_3)_2$ and $PdCl_2$(dppf).

3. The method of claim 1 wherein the base is a member selected from the group consisting of NaOH, KOH, $K_2CO_3$, $KHCO_3$, and $NaHCO_3$.

4. The method of claim 1 wherein the palladium compound is $Pd(PPh_3)_4$ and the base is NaOH.

5. The method of claim 1 wherein step (b) is performed with $BBr_3$.

6. A method for preparing 6-iodoapigenin trimethyl ether 8 comprising the steps of:

(a) demethylating apigenin trimethyl ether 5b to produce 7,4'-dimethoxy-5-hydroxyflavone 6;

(b) reacting 7,4'-dimethoxy-5-hydroxyflavone 6 with a thallium(I) salt in the presence of elemental iodine to produce 7,4'-dimethoxy-5-hydroxy-6-iodoflavone 7;

(c) methylating 7,4'-dimethoxy-5-hydroxy-6-iodoflavone 7 so as to produce 6-iodoapigenin trimethyl ether 8.

7. The method according to claim 6 wherein step (a) is performed with a boron compound.

8. The method according to claim 7 wherein the boron compound is a member selected from the group consisting of boron tribromide and boron trichloride.

9. The method of claim 6 wherein step (b) thallium(I) salt is a member selected from the group consisting of thallium (I) acetate, thallium (I) chloride and thallium (I) bromide.

10. The method of claim 6 wherein step (c) methylation is performed with dimethylsulfate.

11. A method for preparing an 5,7,4'-trimethoxyflavone-3'-boronate 9b comprising reacting 3'-iodo-5,7,4'-trimethoxyflavone 5a with an boronic acid derivative in the presence of a palladium catalyst.

12. The method of claim 11 wherein the boronic acid derivative comprises an alkyl boronic acid derivative or an aryl boronic acid derivative.

13. The method of claim 12 wherein the boronic acid derivative is bis(pinacolato)diboron or pinacolborane.

14. The method of claim 11 wherein the palladium catalyst is a member selected from the group consisting of $PdCl_2$(dppf), $Pd(PPh_3)_4$, $PdCl_2$ and $PdCl_2(PPh_3)_2$.

15. The method of claim 11 wherein the 5,7,4'-trimethoxyflavone-3'-boronate is pinacol 5,7,4'-trimethoxyflavone-3'-boronate.

16. A method for preparing a compound of formula I wherein

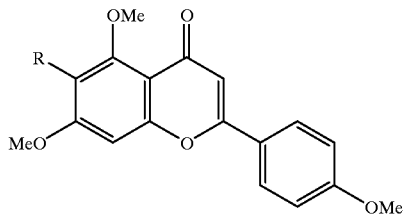

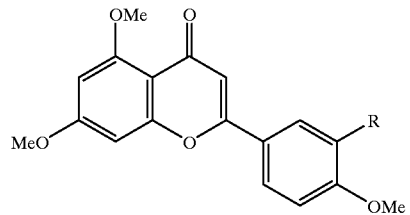

R represents alkyl or aryl, the method comprising reacting an 6-substituted iodo or boronic ester derivative of apigenin with a cross-coupling reagent in the presence of a palladium catalyst.

17. The method according to claim 16 wherein the cross-coupling reagent comprises alkyl- or arylboronic acids, alky- or arylstannane, primary or secondary aliphatic or aromatic amines.

18. The method of claim 16 wherein the palladium catalyst is a member selected from the group consisting of $PdCl_2(dppf)$, $Pd(PPh_3)_4$, $PdCl_2$ and $PdCl_2(PPh_3)_2$.

19. A method for preparing a compound of formula II wherein

R represents alkyl or aryl, the method comprising reacting an 3'-substituted iodo or boronic ester derivative of apigenin with a cross-coupling reagent in the presence of a palladium catalyst.

20. The method according to claim 19 wherein the cross-coupling reagent comprises alkyl- or arylboronic acids, alkyl- or aryistannane, primary or secondary aliphatic or aromatic amines.

21. The method of claim 19 wherein the palladium catalyst is a member selected from the group consisting of $PdCl_2(dppf)$, $Pd(PPh_3)_4$, $PdCl_2$ and $PdCl_2(PPh_3)_2$.

22. 5,7-4'-Trimethoxy-3'-(trimethylstannyl)flavone (9a).

23. Pinacol 5,7-4'-trimcthoxylflavone-3'-boronate (9b).

* * * * *